United States Patent
Schaffer et al.

(10) Patent No.: US 9,367,817 B2
(45) Date of Patent: Jun. 14, 2016

(54) METHODS AND SYSTEMS FOR IDENTIFYING PATIENTS WITH MILD COGNITIVE IMPAIRMENT AT RISK OF CONVERTING TO ALZHEIMER'S

(75) Inventors: James David Schaffer, Vestal, NY (US); Caitlyn Marie Chiofolo, New Hyde Park, NY (US)

(73) Assignee: Koninkijke Philips N.V., Eindhoven (NL)

( * ) Notice: Subject to any disclaimer, the term of this patent is extended or adjusted under 35 U.S.C. 154(b) by 279 days.

(21) Appl. No.: 13/995,284

(22) PCT Filed: Dec. 9, 2011

(86) PCT No.: PCT/IB2011/055584
§ 371 (c)(1),
(2), (4) Date: Jun. 18, 2013

(87) PCT Pub. No.: WO2012/085743
PCT Pub. Date: Jun. 28, 2012

(65) Prior Publication Data
US 2013/0275350 A1    Oct. 17, 2013

Related U.S. Application Data

(60) Provisional application No. 61/424,829, filed on Dec. 20, 2010.

(51) Int. Cl.
*G06N 5/00* (2006.01)
*G06N 99/00* (2010.01)
*G06F 19/00* (2011.01)

(52) U.S. Cl.
CPC ............ *G06N 99/005* (2013.01); *G06F 19/345* (2013.01); *G06F 19/3443* (2013.01)

(58) Field of Classification Search
CPC ........... G06N 5/02; G06N 5/04; G06N 5/048; G06F 17/02
See application file for complete search history.

(56) References Cited

U.S. PATENT DOCUMENTS 7,294,107 B2    11/2007   Simon et al.
2006/0099624 A1    5/2006   Wang et al.
(Continued)

FOREIGN PATENT DOCUMENTS

| WO | 0210456 A2 | 2/2002 |
|---|---|---|
| WO | 2006017153 A2 | 2/2006 |
| WO | 2006135368 A1 | 6/2006 |

OTHER PUBLICATIONS

Pinheiro, P. et al. "A Multicriteria Model Applied in the Diagnosis of Alzheimer's Disease: A Bayesian Network". 2008 11th IEEE International Conference on Computational Science and Engineering. pp. 15-22.
(Continued)

*Primary Examiner* — Stanley K Hill
*Assistant Examiner* — Kalpana Bharadwaj

(57) ABSTRACT

Methods and systems for selecting a cohort group or a patient at risk from a population of patients with mild cognitive impairment. The methods include using a computer configured to perform the steps: receiving normalized learning data from a portion of the population of patients; tuning a set of decision trees on the normalized learning data; receiving patient data from one or more patients of the population, wherein the patient data is independent from the learning data; classifying the patient data with the tuned set of decision trees to obtain patient threshold values; and displaying the patient threshold values.

15 Claims, 12 Drawing Sheets

(56) References Cited

U.S. PATENT DOCUMENTS

| | | | |
|---|---|---|---|
| 2006/0246495 | A1 | 11/2006 | Garrett et al. |
| 2008/0288227 | A1 | 11/2008 | Higgins et al. |
| 2009/0075395 | A1 | 3/2009 | Lee et al. |
| 2011/0257893 | A1* | 10/2011 | Taylor et al. .................. 702/19 |
| 2013/0203061 | A1* | 8/2013 | Kuslich et al. .............. 435/6.12 |

OTHER PUBLICATIONS

Lemsky, C. et al "Identifying Risk for Functional Impairment using cognitive measure: an application of CART modeling" Neuropsychology, 1996, vol. 10, No. 3 368-375—D1).

* cited by examiner

METHODS AND SYSTEMS FOR IDENTIFYING PATIENTS WITH MILD COGNITIVE IMPAIRMENT AT RISK OF CONVERTING TO ALZHEIMER'S

BACKGROUND

In general, the pathology of Alzheimer's Disease (AD) is not fully understood. Clinicians have a long-standing need to develop new therapy options based on pharmaceuticals and other treatments. Further, early detection of the onset of Alzheimer's disease is currently nearly impossible, but would be of great benefit for conducting clinical trials of new therapies.

To demonstrate the efficacy of a therapy in a clinical trial, it is necessary to recruit a population of patients that includes those who are most likely to benefit. Failure to do so greatly reduces the ability of a clinical trial to prove the efficacy of a treatment. This may lead to the rejection of medications or treatments that are effective, but whose effectiveness cannot be demonstrated through statistical means. The adequacy of the clinical trial population is an important factor in developing new therapies for Alzheimer's Disease.

Accurate diagnosis of various conditions of dementia is difficult in clinical practice today. Diagnosis is often attempted using neuropsychological tests (NPT). A wide range of NPTs are known, some borrowed from the intelligence quotient (IQ) domain and others devised specifically for dementias, e.g. ADAS-Cog. The determination of a diagnosis using NPT scores remains difficult or impossible in many circumstances.

Regarding Alzheimer's Disease, a designation known as "mild cognitive impairment" (MCI) has been adopted for clinical use. MCI is not yet an official diagnostic category, e.g. MCI does not have a DSM-IV code. MCI generally requires the presence of at least one impairment of cognitive function that does not seriously compromise a person's ability to function socially and professionally.

Only some of the patients diagnosed as being MCI will progress to Alzheimer's Disease. The conversion from MCI to AD may take up to several years. A means for determining which MCI patients will progress to AD would be of considerable use in the early detection of AD and in following the progress of its pathology.

In addition, clinicians are often faced with the challenge of comprehending the implications of a large number of clinical measurements. These may be performance tests, lab values, metrics derived from images, and the like. Further, there may be historical arrays of the same or similar information that need to be included as context from which important clinical decisions need to be made.

For example, in the evaluation of patients with cognitive complaints, clinicians often employ batteries of NPT tests. These tests attempt to quantify cognitive abilities in many dimensions, e.g. memory, executive control, and language. It is difficult for clinicians to use these arrays of information because of the clutter of data resulting from the large number of NPT tests, as well as the need to review scores across various cognitive dimensions and across time.

US Patent Publication 2006/0099624 discloses a method for providing personalized healthcare to a patient suspect of having or having AD which includes using information fusion or machine learning with heterogeneous data to provide a diagnosis, prognosis or treatment.

In general, these and other methods in the field can suffer from overfitting of the data which may cause incorrect diagnosis of a patient. Incorrect results include false positives and negatives, as well as poor sensitivity or specificity for identifying patients with mild cognitive impairment who are at risk, or in diagnosis.

There is a long-standing need for methods and systems to provide tools for physicians and clinicians which transform and present comparative patient conditions to provide a basis for interpretation, diagnosis and treatment options, as well as for detection of the onset of Alzheimer's disease.

There is a long-standing need for methods and systems to provide tools for physicians and clinicians for selecting a cohort group or a patient at risk of Alzheimer's disease from a population of patients with mild cognitive impairment.

There is a long-standing need for methods and systems to provide tools for physicians and clinicians to monitor the diagnosis, prognosis and course of treatment options in the progression of Alzheimer's disease.

BRIEF SUMMARY

Disclosed herein in one or more exemplary embodiments is a system for personalized diagnosis, treatment, and for identifying patients with mild cognitive impairment at risk of converting to Alzheimer's Disclosed herein in one or more exemplary embodiments are methods for selecting a cohort group or a patient at risk from a population of patients with mild cognitive impairment. The methods include using a computer configured to perform the steps: receiving normalized learning data from a portion of the population of patients; tuning a set of decision trees on the normalized learning data; receiving patient data from one or more patients of the population, wherein the patient data is independent from the learning data; classifying the patient data with the tuned set of decision trees to obtain patient threshold values; and displaying the patient threshold values.

The methods also include selecting a cohort group or a patient at risk from the population, wherein the selected cohort group or patient at risk is outside the portion of the population that supplied the learning data, and the cohort group or patient at risk is selected for a medical purpose based on the patient threshold values. The cohort group or patient at risk may be selected for the medical purpose of: performing a clinical study relating to Alzheimer's, treating the patients for Alzheimer's, determining a drug to be administered for treating the patients for Alzheimer's, determining a dosage of a drug to be administered for treating the patients for Alzheimer's.

Furthermore, tuning the set of decision trees may be used to determine a numerical range of a number of boosting iterations, a numerical range of a minimum number of patients in a node to be split, and a numerical range of a maximum node depth, thereby providing a set of decision trees having at least 80% accuracy, or 85% accuracy for the learning data.

Also, the learning data may include a first learning data set obtained from the population of patients with mild cognitive impairment, wherein the patients from whom the first learning data set is obtained are observed to convert to Alzheimer's within six months to two years after the first learning data set is obtained, the first learning data set comprising neuropsychological test results and biomarkers; and a second learning data set obtained from patients in the population of patients with mild cognitive impairment who do not convert to Alzheimer's within six months to two years after the second learning data set is obtained, the second learning data set comprising neuropsychological test results and biomarkers.

Examples of biomarkers include data from medical imaging, PET imaging, FDG-PET, or MRI imaging. In certain embodiments, the biomarkers are molecular biomarkers, CSF biomarkers, or blood sample biomarkers. Other data includes genetic tests, or microarrays, such as tests for alleles of ApoE, Factor II, Factor III, or Factor IV, among others.

In certain aspects, the patient data may include data obtained from patients in the population of patients with mild cognitive impairment, and neuropsychological test results and biomarkers.

Some embodiments further provide a computer programmed to perform a method for selecting a cohort group or a patient at risk from a population of patients with mild cognitive impairment. The method may include receiving normalized learning data from a portion of the population of patients; tuning a set of decision trees on the normalized learning data; receiving patient data from one or more patients of the population, wherein the patient data are independent from the learning data; classifying the patient data with the tuned set of decision trees to obtain patient threshold values; and displaying the patient threshold values.

In certain aspects, classifying the patient data with the tuned set of decision trees to obtain patient threshold values may be cross validating the patient data with the tuned set of decision trees to obtain patient threshold values, where the cross validating may be k-fold and k is 2, 3, 4, 5, 6, 7, 8, 9, 10, or greater. In certain embodiments, cross validating the patient data is five-fold.

In an exemplary embodiment, a computer-readable storage medium is disclosed which may contain instructions operable to perform a method for selecting a cohort group or a patient at risk from a population of patients with mild cognitive impairment.

In additional aspects, methods are included for increasing the efficacy of a drug treatment protocol for Alzheimer's in a patient. The method may include providing initial patient data; classifying the initial patient data with a set of decision trees to obtain initial patient threshold values; administering the drug to the patient; providing follow-up patient data; and classifying the follow-up patient data with a set of decision trees to obtain follow-up patient threshold values; wherein a decrease of the follow-up patient threshold values indicates a need to continue the drug administration; and wherein an increase of the follow-up patient threshold values indicates a need to discontinue the drug administration.

The methods and systems of this disclosure may advantageously provide anxiety relief for patients who exhibit the pattern associated with MCI, but do not fit the pattern of conversion to AD.

Some of the methods and systems of this disclosure may allow therapeutic drug, protocol and dosage selection to be monitored and evaluated in the progress of a pathology.

Also, the risks of over or under prescribing, i.e. giving a therapy to patients unlikely to benefit, or failing to give a therapy to patients needing it, may be reduced.

In some aspects, the methods and systems of this disclosure may allow therapeutic drug, protocol and dosage selection to be personalized to a particular patient's needs.

Furthermore, this disclosure includes methods for selecting or recruiting patients who are likely to show AD symptoms in a certain time horizon, for example one year or longer. These embodiments may advantageously be used to strengthen the conclusions of a clinical trial or increase the statistical power of a clinical trial. By selecting a cohort group or a patient at risk of Alzheimer's Disease from a population of patients with mild cognitive impairment, exemplary embodiments may provide significant improvement in the results of a clinical trial by increasing the distinction between a treatment arm and a placebo arm of the trial.

In some aspects, this disclosure provides methods and systems for transforming and understanding comparative patient clinical results to provide a basis for diagnosis and treatment options, as well as for detecting the onset of Alzheimer's disease.

In further embodiments, this disclosure provides methods and systems to monitor the course of treatment options in the progression of Alzheimer's disease.

In one exemplary embodiment, methods and systems based on patient threshold values are disclosed. A patient threshold value method of this disclosure may employ the results of a battery of NPT scores. The NPT scores can be pre-processed or converted to z-scores to remove certain biases.

In some embodiments, the patient threshold values may be displayed in a receiver operating curve.

In further embodiments, selected clinical data can be displayed as a magnitude profile of measurements as a single entity for a single patient.

In certain embodiments, a time course display may be used to show how a clinical profile changes across time. An ensemble of selected measurements that together capture a clinically important feature or domain can be displayed to show how it changes across time. In various alternative embodiments, the display includes suitable confidence bounds on the time-course of a measurement in order to ascertain if the changes observed are clinically meaningful.

In further embodiments, a heatmap display can be used that enables rapid assimilation of a large number of measurements and their change across time.

To assist those of skill in the art in making and using the disclosed embodiments, reference is made to the appended figures. Additional features, functions, and advantages of the disclosed systems and methods will be apparent from the more detailed description that follows, in conjunction with the appended figures.

DETAILED DESCRIPTION

As set forth herein, exemplary embodiments of this disclosure provide a range of methods and systems for physicians and clinicians which transform and present comparative patient conditions to provide a basis for interpretation, diagnosis and treatment options, as well as for detection of the onset of Alzheimer's disease.

In additional exemplary embodiments, this disclosure provides a range of methods and systems for physicians and clinicians for selecting a cohort group or a patient at risk of Alzheimer's disease from a population of patients with mild cognitive impairment.

Further exemplary embodiments of this disclosure provide a range of methods and systems for physicians and clinicians to monitor the diagnosis, prognosis and course of treatment options in the progression of Alzheimer's disease.

It will further be appreciated that while particular examples are enumerated herein to describe exemplary embodiments, the examples are described for illustration only, and are not limiting to the disclosure. Many variations, substitutes, and equivalents will be apparent to those contemplating the embodiment(s) disclosed herein.

Figure 1A:
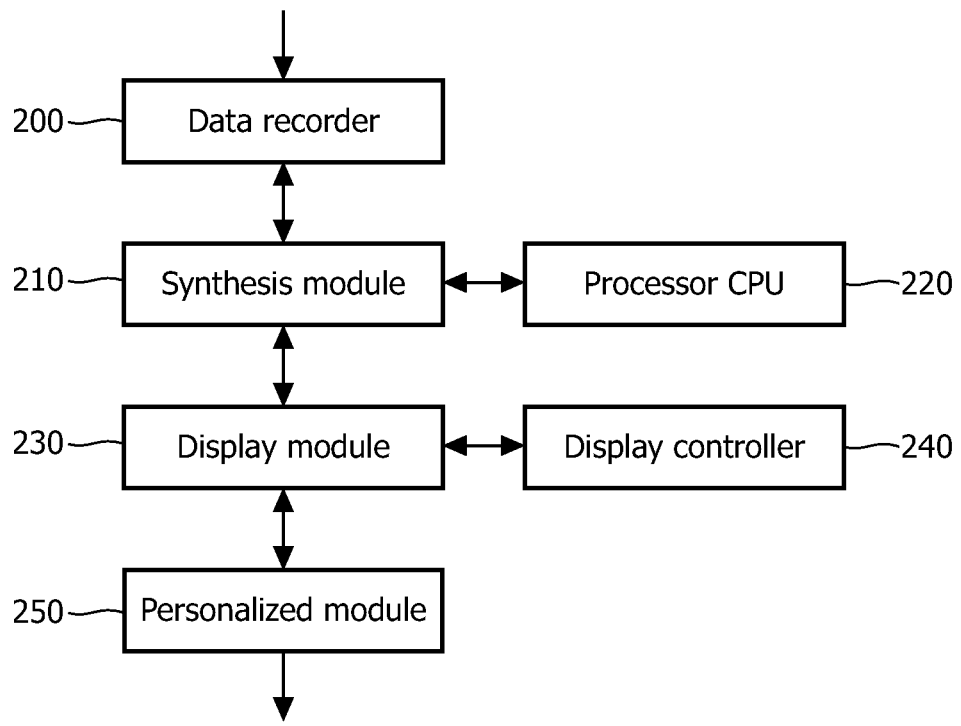
FIG. 1A shows a block diagram of a system for personalized diagnosis, treatment, and identifying patients with mild cognitive impairment at risk of converting to Alzheimer's.

As shown in FIG. 1A, a system for personalized diagnosis, treatment, and identifying patients with mild cognitive impairment at risk of converting to Alzheimer's includes, among other things, a synthesis module 210 connected to a data recorder 200 and a processor CPU 220. The synthesis module 210 obtains patient data from the data recorder 200. The data recorder 200 is adapted to receive and store patient data including, for example, clinical trial data, clinical test results, NPT test results, genetic information, medical history data, medical imaging data, and biomarker data. The synthesis module 210 includes means for transforming patient data and combining the transformed data with other patient data by one or more transformation methods. The means for transforming patient data include a computer-readable storage medium containing instructions operable to perform one or more methods for transforming patient data. The methods for transforming patient data include, for example, learning techniques, classification methods, random forests, support vector machines, k nearest neighbors, statistical methods, vector analysis, decision analysis, decision trees, Bayesian classifiers, genetic classifiers, pattern discovery methods, as well as methods for numerical classification, cluster analysis, orthogonal transformation, and matrix decomposition methods. The transformations of patient data include, for example, transformations of raw scores to correct for biases, conversion to Z-scores, and generating confidence intervals.

The synthesis module 210 uses the processor CPU 220 in various steps of the transformation methods. The processor CPU 220 can be a personal computer, a laptop, a medical computer, a data management computer, or a server. The synthesis module 210 will output patient data, transformed patient data, or combinations of patient data and transformed patient data to the display module 230.

The display module 230 includes display controller 240 which has a graphical user interface for an operator who may be a physician or health care provider. The display module 230 includes a display device for displaying patient data, transformed patient data and combined data. The display device may be any digital or analog display device including a flat panel display, or any display used on a cellular device, smart phone, PDA, personal tablet or pad device, or computer. The display controller 240 further includes input devices such as keyboard and mouse for inputting operator selections through the user interface. Operator selections at the display controller 240 may trigger a change in the display by communicating to the synthesis module 210 a desired change in the patient data, transformed patient data or combined data.

The personalized module 250 communicates with the display module 230 to determine and display personalized patient information. The personalized module 250 may include a display device such as a flatpanel display. The personalized module 250 includes methods for comparing individual patient data obtained at different times to monitor progress of a pathology. The personalized module 250 includes methods for determining treatment options for an individual patient based on transformed patient data or combined data contained in the display module 230.

Operator selections at the display controller 240 may be used to transform clinical data to a form that can be displayed at the display controller 240 or at the personalized module 250 to provide evidence for diagnosis decisions by the operator. The display controller 240 may contain methods for making a diagnosis based on clinical data and individual patient data, optionally combined with confidence intervals and other criteria input by the operator.

The processor CPU 220 and other modules of the system may contain methods including a set of instructions stored in a computer-readable storage device such as flash memory, RAM memory, ROM memory, a magnetic disk, a CD, or a DVD. Connections from the processor CPU 220, as well as from and between other modules and devices of the system may include hardwire, USB, networking, wireless, Ethernet, LAN, WAN, Wi-Fi, Bluetooth™, AirPort™, or IEEE 802.11n or IEEE 802.11a/b/g wireless devices.

Some methods are disclosed herein to support the rapid comprehension of the clinical importance of an array of clinical information. In some cases, the clinical information is a battery of neuropsychological tests (NPT). The graphical display and methods disclosed herein apply equally well to other types of data and to combinations of datatypes.

A decision aid is also provided that combines the test scores from a battery of neuropsychological tests and produces a patient threshold value. The patient threshold value and an accompanying ROC curve can provide a way of determining a diagnosis, prognosis, or likelihood of conversion to Alzheimer's Disease within a period of time such as one year for patients previously diagnosed with mild cognitive impairment.

A successful clinical trial of a putative AD therapy may depend sensitively on the recruitment of patients. If the trial includes too many patients who do not suffer from the AD pathology, or whose pathology has progressed beyond the point where the therapy can be of immediate benefit, the statistics of the trial outcomes may fail to convincingly demonstrate the benefit.

Figure 1B:
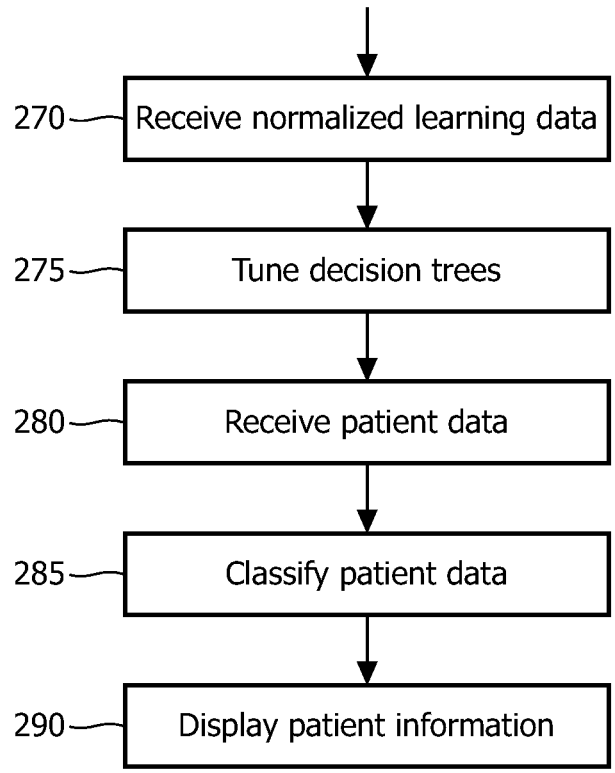
FIG. 1B shows a flow chart for a system for identifying patients with mild cognitive impairment at risk of converting to Alzheimer's.

As shown in FIG. 1B, a flow chart for a system for identifying patients with mild cognitive impairment at risk of converting to Alzheimer's includes, among other things, a step of receiving normalized learning data 270. The normalized learning data is used in a step of tuning a set of decision trees 275. After a step of receiving patient data 280, the set of tuned decision trees is used in a step of classifying the patient data 285. The step of step of classifying the patient data 285 provides patient threshold values which are used in a step of displaying patient information 290. The step of displaying patient information 290 includes displaying the patient threshold values, for example, in an ROC curve. The step of displaying patient information 290 optionally includes displaying other patient information including a personalized diagnosis, a personalized treatment plan, a personalized therapeutic drug, protocol or dosage selection, or a personalized healthcare decision aid.

NPT tests are subject to uncertainty with respect to test-retest reliability, learning effects, and biases for factors like age, gender and years of education. NPT test scores can be converted to z-scores, i.e. scores reflecting the number of standard deviations from the mean of a suitable normalizing cohort.

Tuning a set of decision trees on normalized learning data may include using multiple splits of the learning data to obtain upper and lower cut-off scores for the NPT test scores which result in the highest accuracy with respect to the learning data. Tuning a set of decision trees on normalized learning data may further include independently varying the number of boosting iterations, the minimum number of patients in a node to be split, and the maximum node depth.

Tuning the set of decision trees may be used to determine a numerical range of a number of boosting iterations, a numerical range of a minimum number of patients in a node to be split, and a numerical range of a maximum node depth. The range of the number of boosting iterations can be 25 or greater, 50 or greater, 100 or greater, up to 200, or from 25 to 200, or from 50 to 200, or from 25 to 75. The range of the minimum number of patients in a node to be split may be from 12 to 40, or may be 18, or 24, or 30, or 36. The range of the minimum number of patients in a node to be split may be from 12 to 40, or from 18 to 40, or from 24 to 40, or from 30 to 40, or from 12 to 40, or from 12 to 36, or from 18 to 30. The range of the maximum node depth can be from 6 to 15, or may be 8, 10, or 12.

Such exemplary embodiments which include a tuned set of decision trees advantageously avoid the problem of overfitting the learning data, and therefore increase the ability to provide a correct classification or diagnosis of a patient.

In an exemplary patient threshold value method, the vector of test scores may be passed through a set of decision trees. The set of decision trees may be tuned for making a diagnostic classification of patients who are stable MCI and will not convert to AD, and a diagnostic classification of patients who are MCI and will convert to AD within one year.

The vector of test scores may be passed through a set of tuned decision trees to determine a patient threshold value, n. The patient threshold value, n, is the number of decision trees in the set of tuned decision trees that classify the patient as an MCI to AD converter. The patient threshold value may vary from zero up to the total number of decision trees in the set of tuned decision trees.

For example, the patient threshold value may be the number of decision trees in the set of decision trees that classify the patient as a converter to Alzheimer's, and the number of decision trees in the set of decision trees may be the number of boosting iterations. The patient threshold value may range from zero up to the number of boosting iterations.

The patient threshold values for a group of patients may be displayed as an ROC curve. An ROC curve shows the true positive rate and the false positive rate that may be expected of a decision threshold for any value of the patient threshold value.

In certain aspects, the learning data can include test and retest results obtained over a period of time, for example, six months, or one year, or two years, or three years, or longer.

Selection of a subset of tests from a battery of a large number of NPT tests can be used as the learning data in a method for identifying a cohort group or a patient at risk from a population of patients with mild cognitive impairment. It is in general unpredictable which subset of tests from a battery of a large number of NPT tests will achieve the highest accuracy when the results based on the learning data are cross validated with other patient data.

Figure 2:
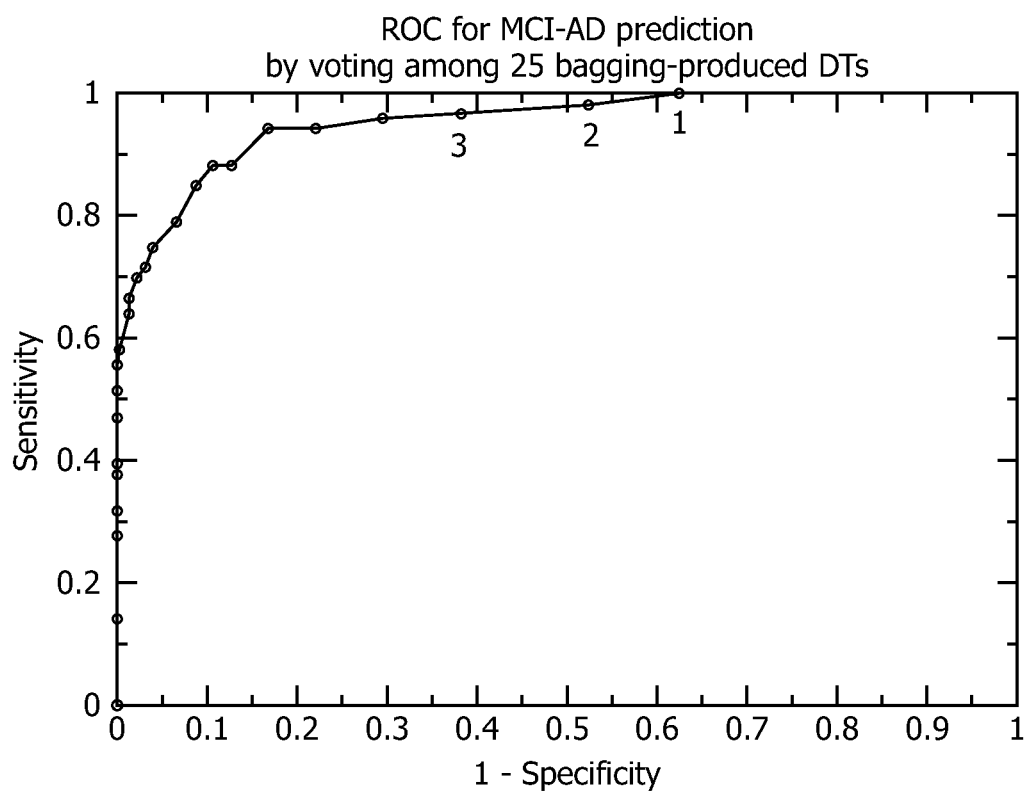
FIG. 2 shows a DT-ROC display of patient threshold values for patients from the Alzheimer's Disease Neuroimaging Initiative (ADNI) multisite, multi-study program of 800 subjects, including 200 elderly controls, 400 mild cognitive impairment subjects, and 200 Alzheimer's subjects. The DT-ROC display represents the true positive rate and the false positive rate that may be expected for a patient threshold value of n. The x-axis represents the quantity "1 minus specificity," and the y-axis represents the quantity "sensitivity." The patient threshold value of n is represented by the points on the graph in sequential order, where the point farthest to the right is n=1, the next point to the left is n=2, the next point to the left is n=3, and so forth.

In an exemplary patient threshold value method, an ROC curve as shown in FIG. 2 can be generated and displayed. FIG. 2 shows an embodiment of a decision tree ROC display (DT-ROC) of patient threshold values for patients from the Alzheimer's Disease Neuroimaging Initiative (ADNI) study of 800 subjects, including 200 elderly controls, 400 mild cognitive impairments, and 200 Alzheimer's. The ADNI database is described at www.loni.ucla.edu/ADNI. The DT-ROC display represents the true positive rate and the false positive rate that may be expected for a patient threshold value of n. The x-axis represents the quantity "1 minus specificity," and the y-axis represents the quantity "sensitivity."

In a further exemplary patient threshold value method for AD, five-fold cross validation was used. The accuracy for the learning data was 87.4%, and the overall accuracy for patient data with five-fold cross validation was 70.5%.

In a further exemplary patient threshold value method for AD, FDG-PET imaging markers were used. The accuracy for the learning data was 86.2%, and the overall accuracy for patient data with five-fold cross validation was 74.4%.

A personalized module display for an individual patient can be based on individual patient data viewed in light of a DT-ROC display such as the one shown in FIG. 2. In some embodiments, a personalized patient threshold value can be used to formulate and display personalized treatment plan options and personalized healthcare decision aids.

In an exemplary patient threshold value method, four personalized healthcare options can be displayed.

Personalized healthcare option 1: Advise the MCI patient not to be concerned that AD is imminent. For a patient with a patient threshold value of zero, the DT-ROC curve shows that no patient who is likely to convert to AD would be so advised.

Personalized healthcare option 2: Prescribe a safe pharmaceutical therapy with a minimum risk for over-prescription. For a patient with a patient threshold value greater than or equal to one, the DT-ROC curve shows that all those who need the therapy will have it, therefore sensitivity=100%. In addition, 62% of stable MCI patients will also receive the therapy (over-prescription).

Personalized healthcare option 3: Prescribe a therapy with more serious risk for over-prescription. For a patient with a patient threshold value greater than or equal to ten, the DT-ROC curve shows that this can be expected to reduce the over-prescription from 62% to about 7%, while failing to prescribe it for about 20% of those who might benefit, therefore sensitivity=80%.

Personalized healthcare option 4: Include patient in a clinical trial for a putative AD-therapy. For a patient with a patient threshold value greater than or equal to seventeen, the DT-ROC curve shows that all admitted patients are likely to convert to AD in one year if untreated. About 55% of actual at-risk patients will meet this criterion. This selection has a high probability of producing a significant difference between the placebo and treatment arms of a clinical trial within a reasonable time.

A graphical display and method are further provided as an option to support the rapid comprehension of the clinical import of an array of clinical information. In some instances, the clinical information is a battery of neuropsychological tests (NPT). The graphical display and method apply equally well to other types of data and to combinations of data types.

The displays of this disclosure are designed to ease the task of comprehending a collection of data that may include several different measures collected together, and especially where the ensemble may be repeated across time, including many variations. Furthermore the individual measurements may have their own statistical properties such as test-retest reliability.

The features characterizing displays of this disclosure include: (a) presentation of a profile of measurements as a single entity, (b) an ability to observe how this profile changes across time, (c) presentation of ensembles of measurements that together capture a clinically important feature or domain, and how they change across time, (d) an ability to view suitable confidence bounds on the time-course of any measurement in order to ascertain if the changes observed are clinically meaningful, and (e) a heatmap display that enables rapid assimilation of a large number of measurements and their changes across time.

In certain methods of this disclosure, example clinical data were pre-processed by correcting for the effects of gender, age, race, and years of formal education, as appropriate, and by inverting some measures so that higher scores always indicate better cognitive performance, as well as converting to Z-scores based on the ADNI normal cohort. While not essential to this disclosure, these pre-processing steps may assist the visualization. Nevertheless, un-normalized or raw scores, and scores with different up/down interpretations could also be displayed.

In one exemplary embodiment, a magnitude display is disclosed. An optional magnitude display provides a visualization of the entire NPT profile of a patient relative to the normal range. Repeated assessments may be shown as additional profiles superimposed, optionally in different colors, with increasing plot symbol size for more recent assessments. The headers in these illustrations may show only the patient's ID code (RID), age, sex, and the diagnosis history. In clinical use, these headers may include any other demographic or medical history characteristics deemed pertinent. Another feature of this display is the order of the tests along the x-axis. Tests have been sorted in an order derived from a sample of the most severely cognitively compromised of the Alzheimer's patients in the ADNI study, and calculated to place leftmost those tests that ranked highest in deviations from normal when averaged across all repeat visits. The sought-after effect is that, as patients exhibit increasing decline of the Alzheimer's type, their profiles will tend to be lower on the left.

Figure 3:
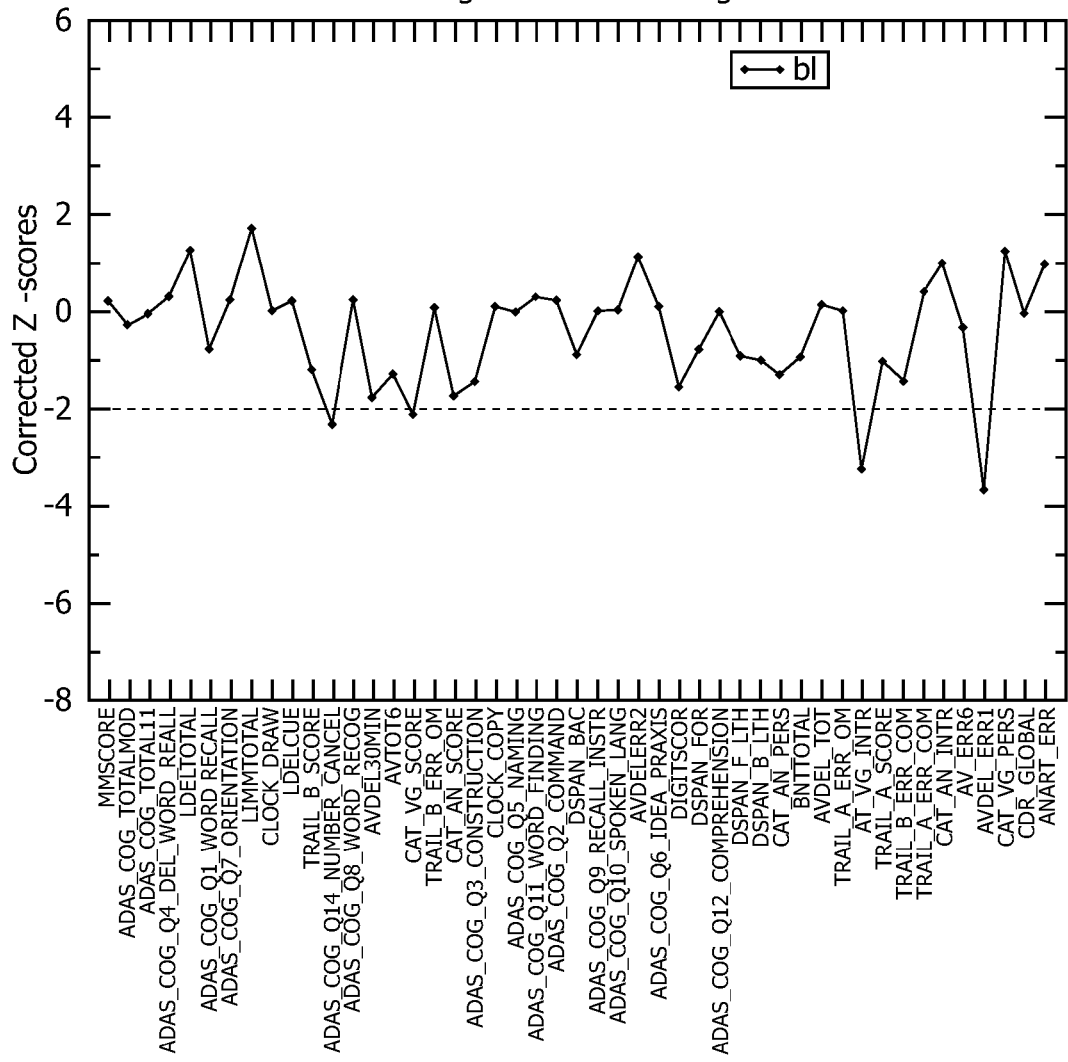
FIG. 3 shows an embodiment of a magnitude display of corrected Z-scores for an individual patient's selected NPT tests at the date of baseline or initial assessment. The magnitude display represents a patient (RID 223) who was assessed as clinically normal (NL).

Referring to FIG. 3, an embodiment of a magnitude display of corrected Z-scores for an individual 81 year old female patient's selected NPT tests at the date of baseline or initial assessment is shown. This magnitude display represents a patient (RID 223) who was assessed as clinically normal (NL). The majority of her test scores were within the normal range, 95% confidence interval −2 to +2, with four exceptions. The selected NPT tests depicted in FIG. 3 were from left to right:

MMSCORE
ADAS_COG_TOTALMOD
ADAS_COG_TOTAL11
ADAS_COG_Q4_DEL_WORD_REALL
LDELTOTAL
ADAS_COG_Q1_WORD RECALL
ADAS_COG_Q7_ORIENTATION
LIMMTOTAL
CLOCK_DRAW
LDELCUE
TRAIL_B_SCORE
ADAS_COG_Q14_NUMBER_CANCEL
ADAS_COG_Q8_WORD_RECOG
AVDEL30MIN
AVTOT6
CAT_VG_SCORE
TRAIL_B_ERR_OM
CAT_AN_SCORE
ADAS_COG_Q3_CONSTRUCTION
CLOCK_COPY
ADAS_COG_Q5_NAMING
ADAS_COG_Q11_WORD_FINDING
ADAS_COG_Q2_COMMAND
DSPAN_BAC
ADAS_COG_Q9_RECALL_INSTR
ADAS_COG_Q10_SPOKEN_LANG
AVDELERR20
ADAS_COG_Q6_IDEA_PRAXIS
DIGITSCOR
DSPAN_FOR
ADAS_COG_Q12_COMPREHENSION
DSPAN_F_LTH
DSPAN_B_LTH
CAT_AN_PERS
BNTTOTAL
AVDEL_TOT

TRAIL_A_ERR_OM
AT_VG_INTR
TRAIL_A_SCORE
TRAIL_B_ERR_COM
TRAIL_A_ERR_COM
CAT_AN_INTR
AV_ERR6
AVDEL_ERR1
CAT_VG_PERS
CDR_GLOBAL
ANART_ERR

Figure 4:
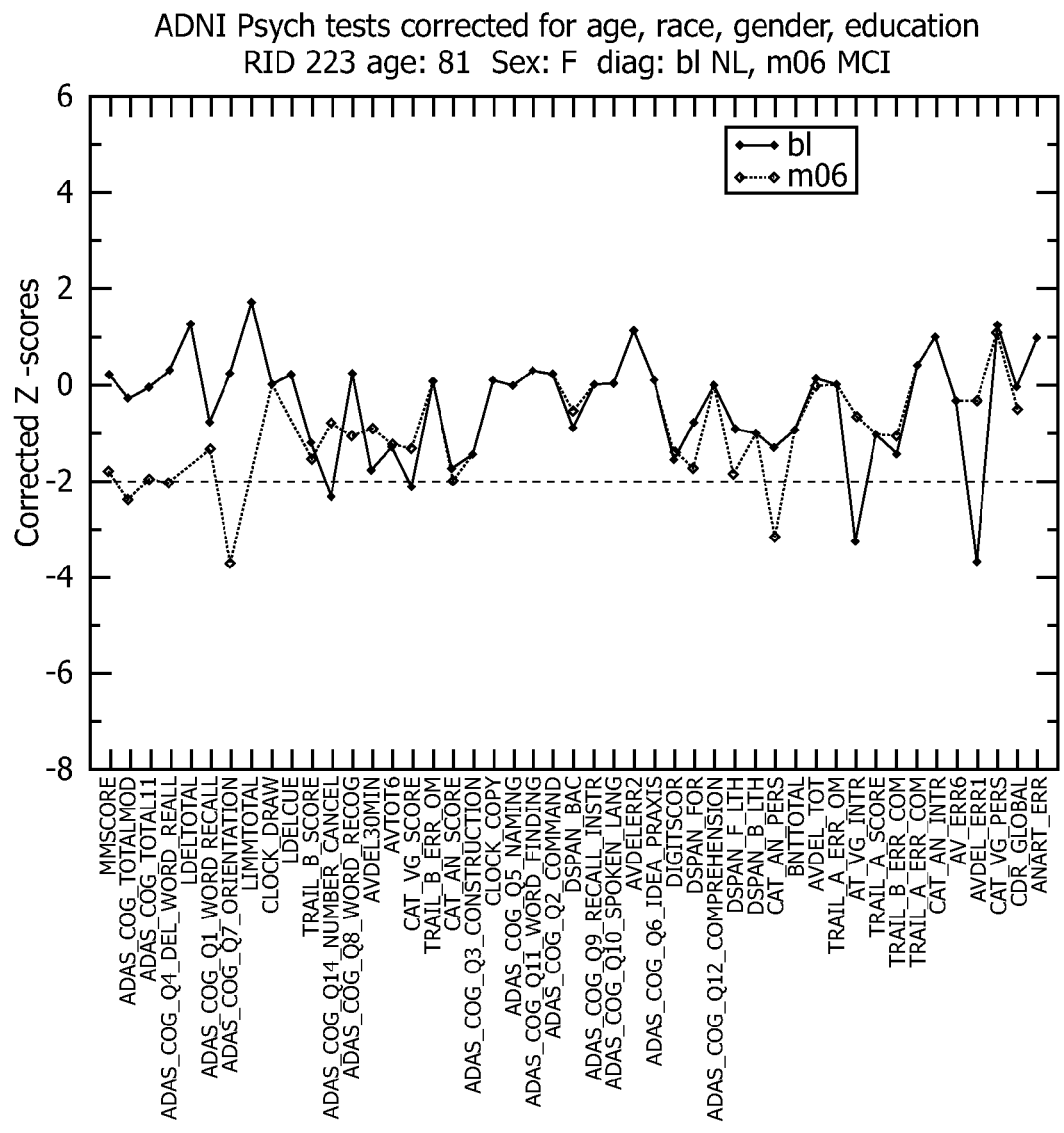
FIG. 4 shows an embodiment of a magnitude display of corrected Z-scores for an individual patient's selected NPT tests six months after the baseline or initial assessment, displayed along with the same profile at baseline. The magnitude display represents a patient (RID 223) who was assessed with mild cognitive impairment.

Referring to FIG. 4, an embodiment of a magnitude display of corrected Z-scores for the same individual patient's selected NPT tests six months after the baseline or initial assessment is shown relative to baseline scores. This magnitude display represents a patient (RID 223) who was assessed with mild cognitive impairment, and her scores on some tests had worsened. It is noted that not all tests were administered at the six month visit. The four exceptions that were outside the normal range at baseline had improved. The selected NPT tests were the same as given above for FIG. 3.

Figure 5:
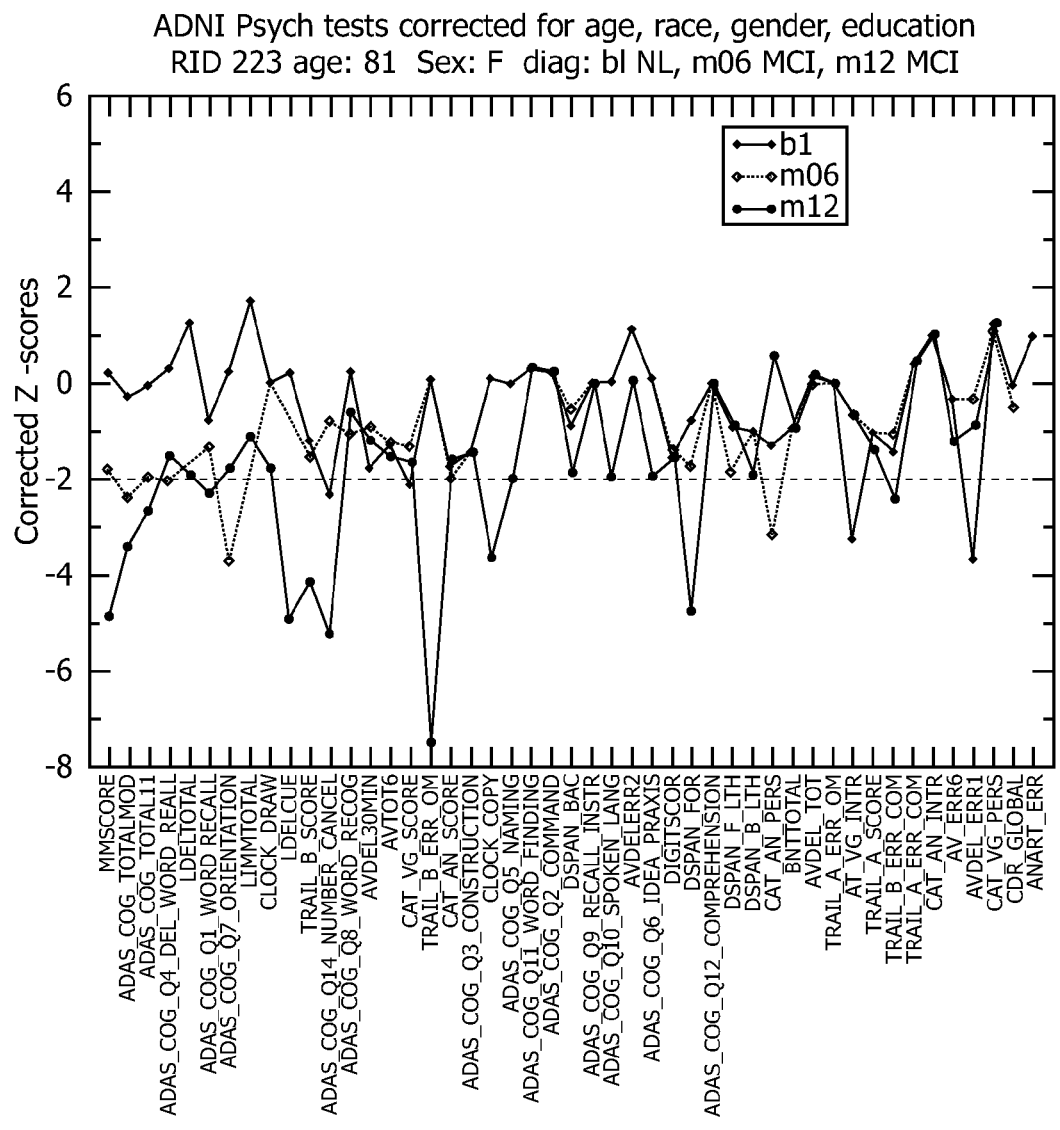
FIG. 5 shows a magnitude display of corrected Z-scores for an individual patient's selected NPT tests twelve months after the baseline or initial assessment, displayed along with the same profile at earlier times. The magnitude display represents a patient (RID 223) with worsening scores.

Referring to FIG. 5, an embodiment of a magnitude display of corrected Z-scores for an individual patient's selected NPT tests twelve months after the baseline or initial assessment is shown relative to previous scores. This magnitude display represents a patient (RID 223) with worsening scores on several tests, including the MMSE and two ADAS-Cog totals (first three on the x-axis) and the logical memory tests (#5, #8, #10). The selected NPT tests were the same as given above for FIG. 3.

Figure 6:
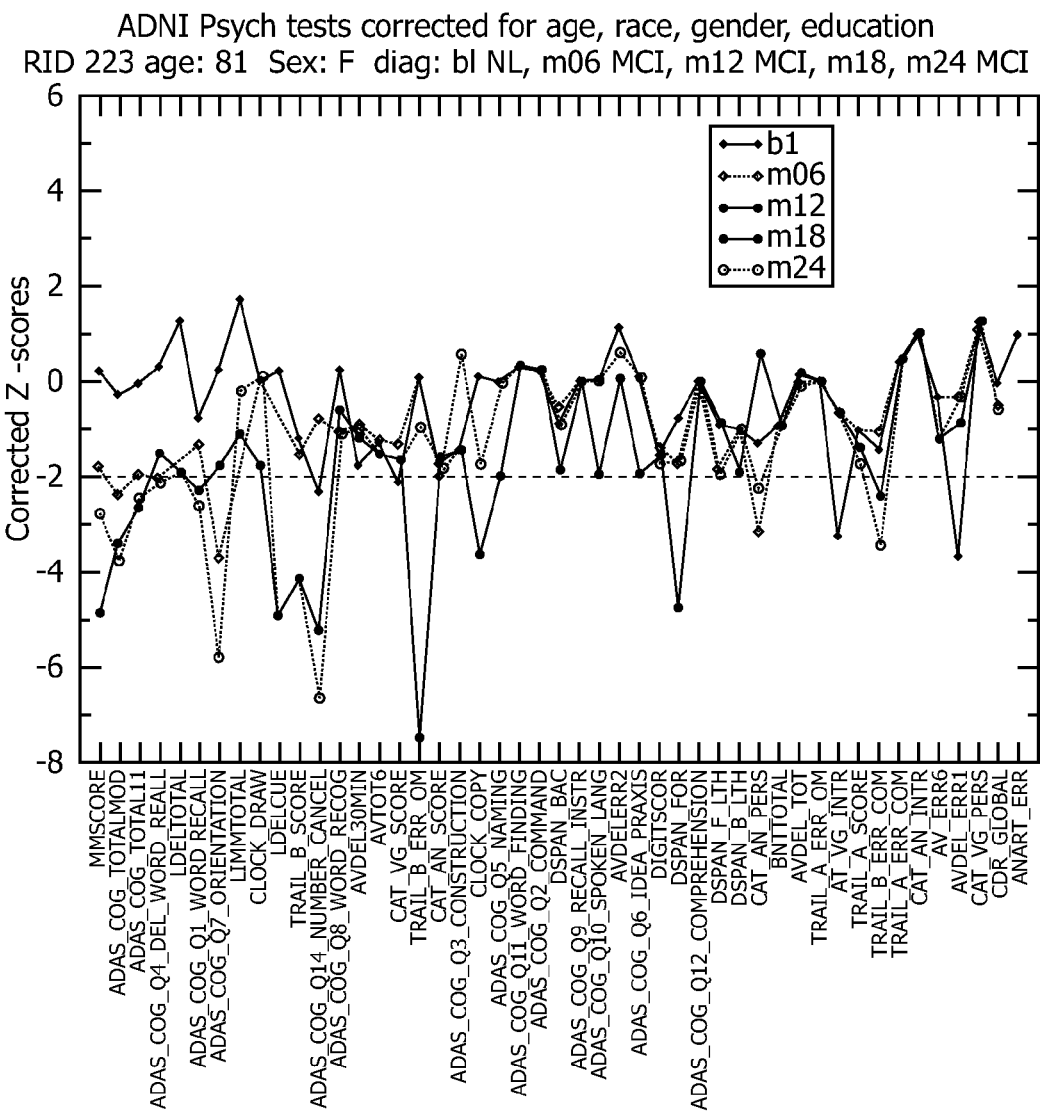
FIG. 6 shows a magnitude display of corrected Z-scores for an individual patient's selected NPT tests twenty-four months after the baseline or initial assessment, displayed along with the same profile at earlier times. The magnitude display represents a patient (RID 223) with a cognitive profile that is not improved.

Referring to FIG. 6, an embodiment of a magnitude display of corrected Z-scores for an individual patient's selected NPT tests twenty-four months after the baseline or initial assessment is shown relative to previous scores. This magnitude display represents a patient (RID 223) with a general cognitive profile that is not improved. The selected NPT tests were the same as given above for FIG. 3.

Figure 7:
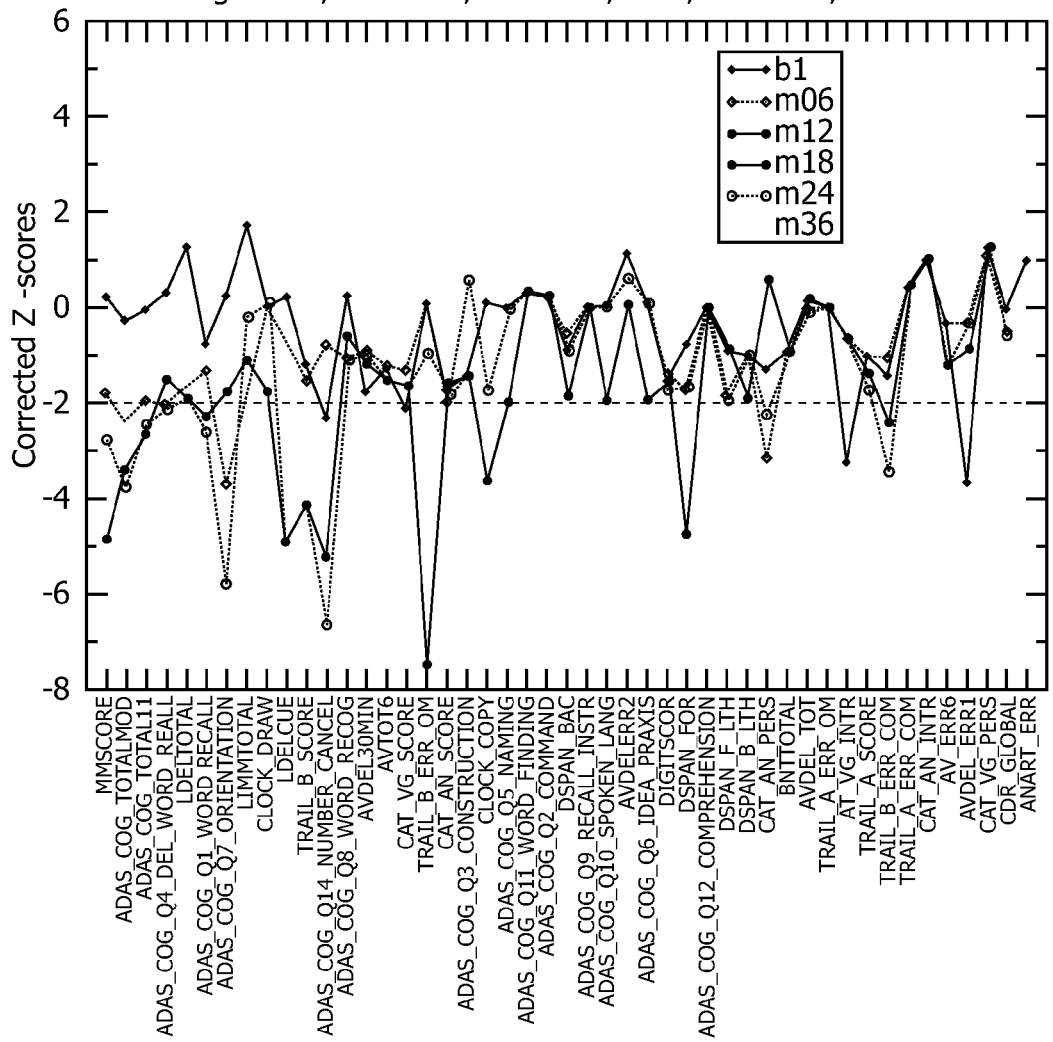
FIG. 7 shows a magnitude display of corrected Z-scores for an individual patient's selected NPT tests thirty-six months after the baseline or initial assessment, displayed along with the same profile at earlier times. The magnitude display represents a patient (RID 223) that progressed to a likely diagnosis of Alzheimer's disease (AD).

Referring to FIG. 7, an embodiment of a magnitude display of corrected Z-scores for an individual patient's selected NPT tests thirty-six months after the baseline or initial assessment is shown relative to previous scores. This magnitude display represents a patient (RID 223) that progressed to a likely diagnosis of Alzheimer's disease (AD). The selected NPT tests were the same as given above for FIG. 3.

As the magnitude display may get cluttered, the magnitude display can optionally be expanded to select a subset of the time course, or a subset of the NPT battery of tests.

The magnitude display has the benefit that the NPT profile can be viewed directly.

The magnitude displays of this disclosure can advantageously be used for performing a diagnosis, determining treatment options, detect the onset of Alzheimer's disease, select a cohort group or a patient at risk of Alzheimer's disease from a population of patients with mild cognitive impairment, or to monitor the diagnosis, prognosis and course of treatment options in the progression of Alzheimer's disease.

In another exemplary embodiment, a time course display is disclosed. A time course display represents time on the x-axis, and shows the results of multiple clinical tests simultaneously. The NPT profile of a certain number of tests is shown in the time course display. The tests for which results are displayed may be selected to measure similar cognitive domains.

Figure 8:
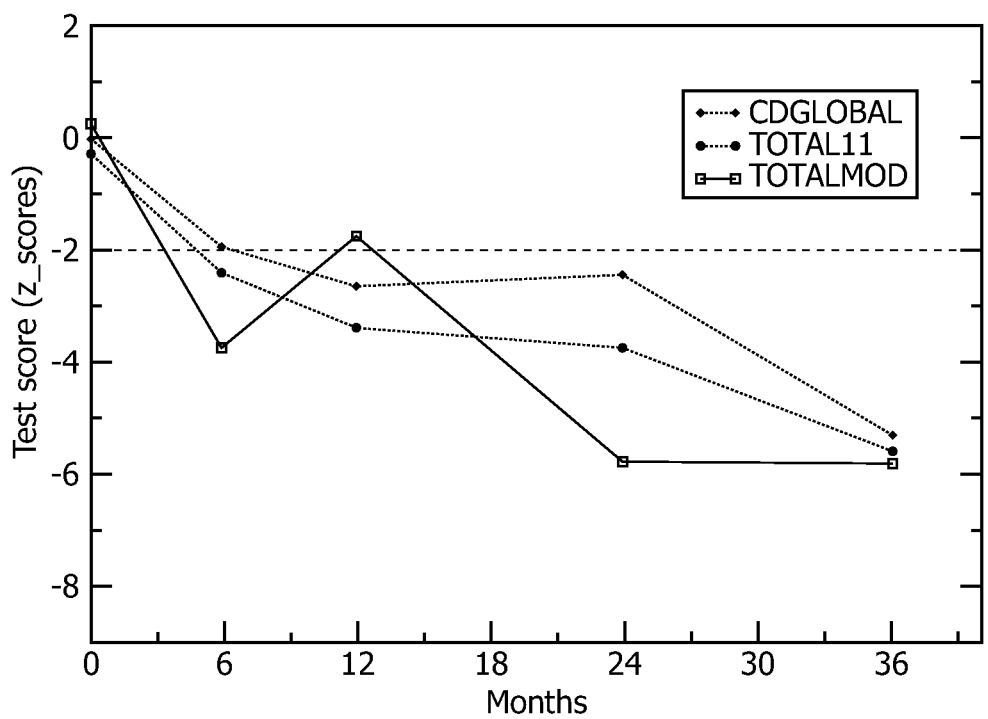
FIG. 8 shows a time course display of three NPT tests for an individual patient. The time course display represents a patient (RID 223) in steady decline.

Referring to FIG. 8, an embodiment of a time course display of three NPT tests for an individual patient is shown. The NPT tests were CDGLOBAL, TOTAL11, and TOTALMOD. This time course display represents a patient (RID 223) in steady decline as shown by test scores that decline from a value of about 0 (zero) at 0 months to a value as low as −6 (minus six) at 36 months. A horizontal line at −2 shows a lower bound of a confidence interval.

Figure 9:
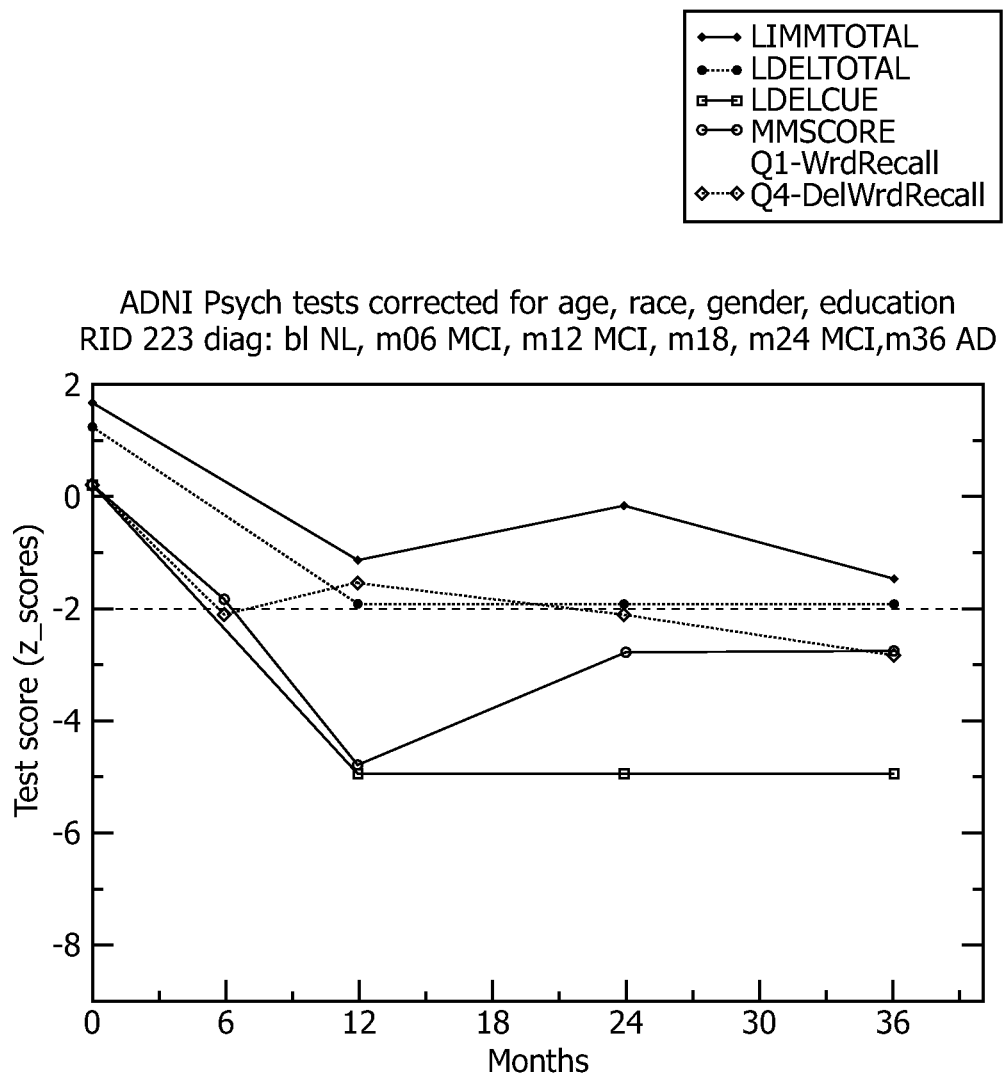
FIG. 9 shows an embodiment of a time course display of six memory domain NPT tests for an individual patient. The time course display represents a patient (RID 223) with early decline followed by leveling.

Referring to FIG. 9, an embodiment of a time course display of six memory domain NPT tests for an individual patient is shown. The NPT tests were LIMMTOTAL, LDELTOTAL, LDELCUE, MMSCORE, Q1-WrdRecall, and Q4-DelWrdRecall. This time course display represents a patient (RID 223) with early decline of test scores followed by leveling.

Figure 10:
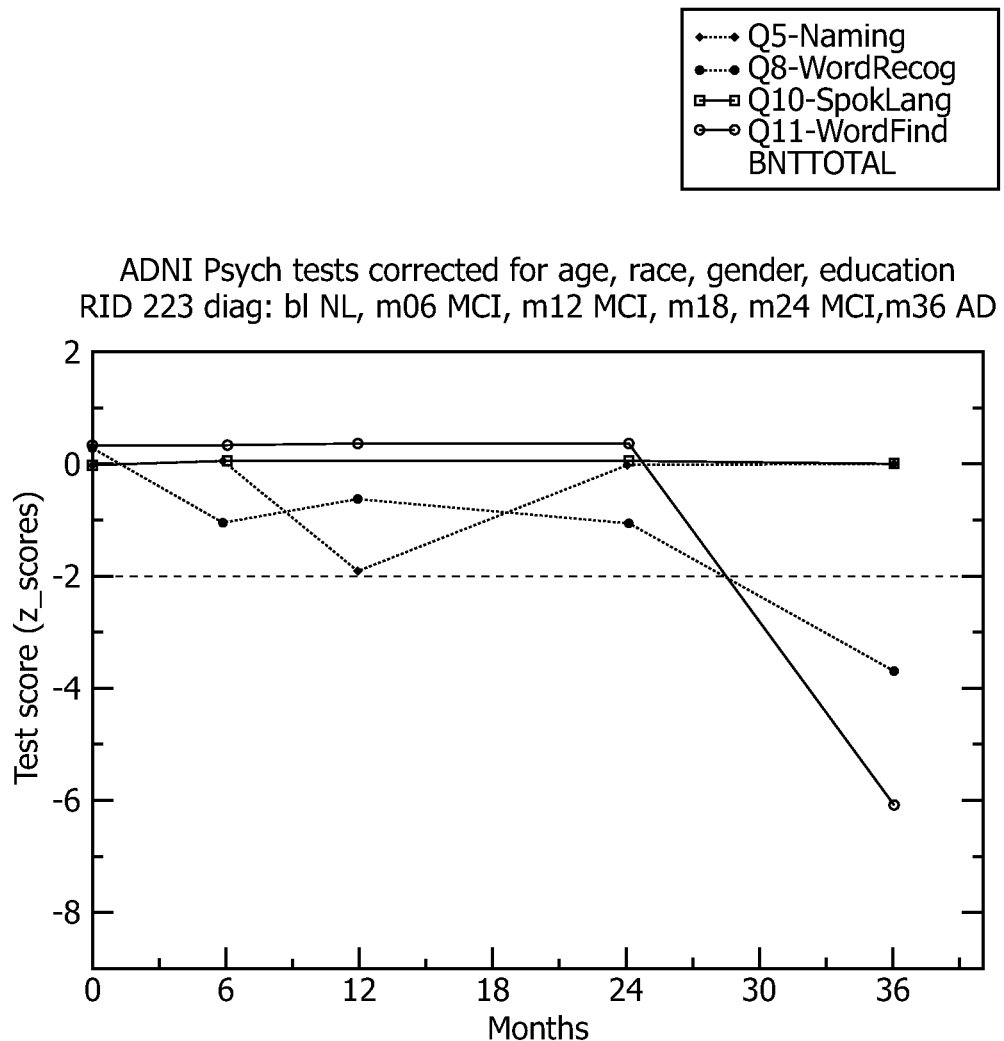
FIG. 10 shows an embodiment of a time course display of five word domain NPT tests for an individual patient. The time course display represents a patient (RID 223) with fluctuations, but no clear trends.

Referring to FIG. 10, an embodiment of a time course display of five word domain NPT tests for an individual patient is shown. The NPT tests were Q5-Naming, Q8-WordRecog, Q10-SpokLang, Q11-WordFind, and BNTTOTAL. This time course display represents a patient (RID 223) with precipitous declines after month 24 in word recognition and word finding.

Figure 11:
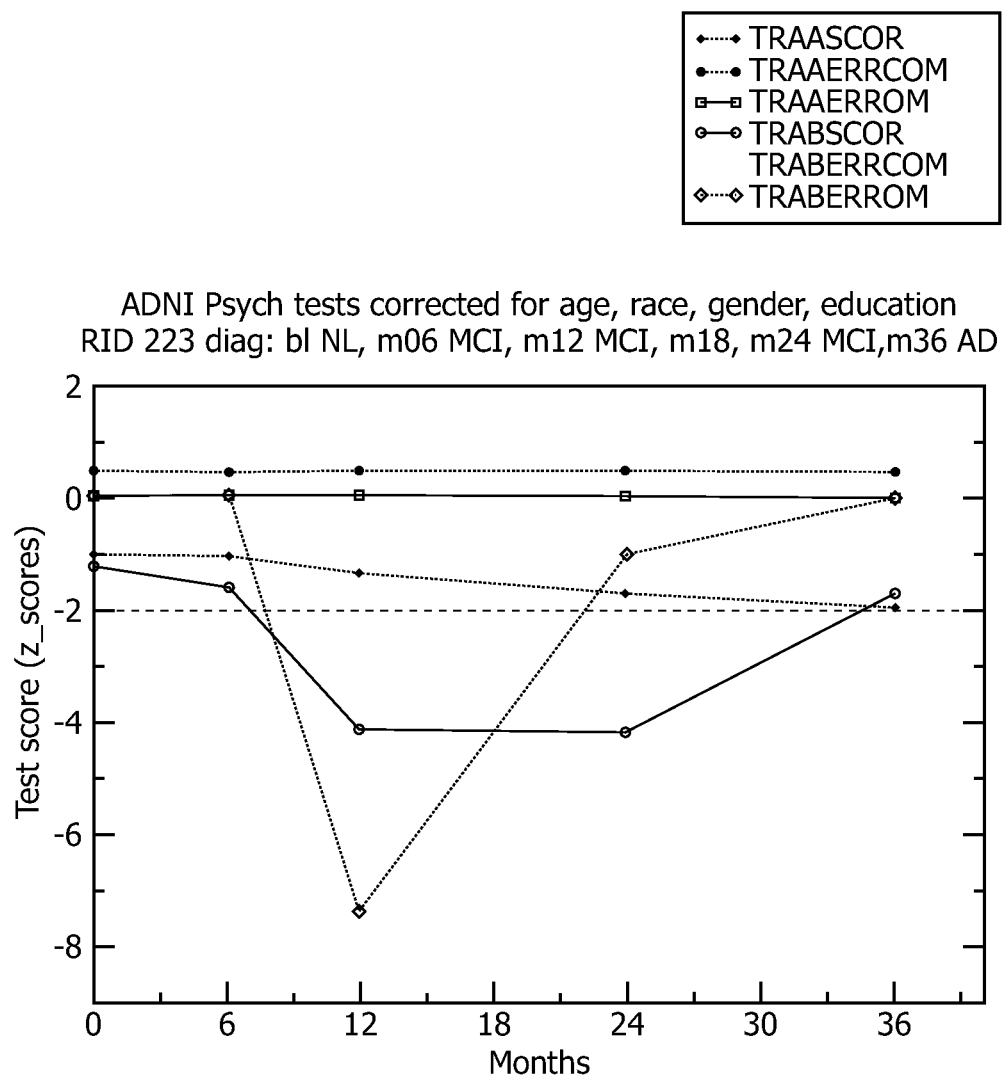
FIG. 11 shows an embodiment of a time course display of six trail making NPT tests for an individual patient with a 95% confidence interval (CI) based on the observed test-retest variations among a cohort of comparable normals. The time course display represents a patient (RID 223) with precipitous declines after month 24 in word recognition and word finding.

Referring to FIG. 11, FIG. 11 shows an embodiment of a time course display of six trail making NPT tests for an individual patient with a 95% confidence interval (CI) based on the observed test-retest variations among a cohort of comparable normals. The NPT tests were TRAASCOR, TRAAERRCOM, TRAAERROM, TRABSCOR, TRABERRCOM, and TRABERROM. This time course display represents a patient (RID 223) with fluctuations, but no clear trends.

Figure 12:
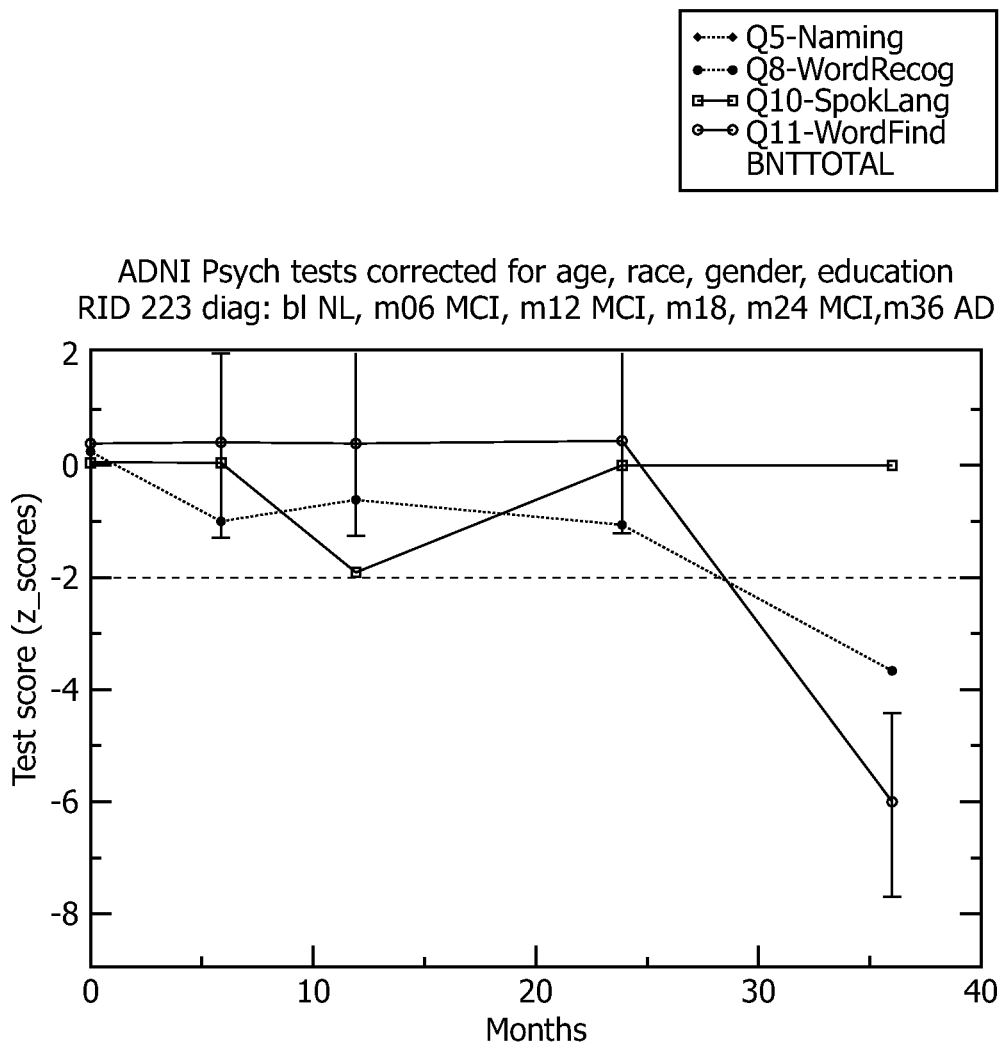
FIG. 12 shows an embodiment of a modified time course display of the word domain cluster of NPT tests for an individual patient. The time course display represents a patient (RID 223) with small variations up to month 24 that were indistinguishable, but a drop at month 36 that was clearly significant.

Referring to FIG. 12, an embodiment of a modified time course display of the word domain cluster of NPT tests for an individual patient is shown. This time course display represents a patient (RID 223) with small variations up to month 24 that were indistinguishable, but a drop at month 36 that was clearly significant. This time course display may be used to ascertain if the drop in the ADAS-Cog Q11 Word Finding item was meaningful. A clickable option produces the modified time course display shown in FIG. 12 wherein each test item has its own CI, and each test item of interest can be displayed separately.

In another exemplary embodiment, a heatmap display is disclosed. A heatmap display of this disclosure represents time on the x-axis. In a heatmap display, all tests are arrayed on the y-axis in the same order as used for a magnitude display. The magnitude of the test Z-scores is color coded according to a mapping. For example, test scores in the confidence interval of normal can be shown in peach to yellow colors, scores between −2 and −4 standard deviations are yellow to green, and scores below −4 are blue to purple. Missing assessments are shown white so they blend into the white background, clearly signaling that they are missing.

In another exemplary embodiment, a heatmap display may have ordering along the y-axis in groups by cognitive domain (1) and for using different coloring/shading schemes with varied bounds for those colors (2). In some embodiments, all tests can be arrayed on the y-axis in the same order as used for a magnitude display, but may also be arrayed in groups by cognitive domain (e.g. memory, speech/language, attention, executive function, and visuospatial). In certain embodiments, test scores in the confidence interval of normal can be shown in shades from one to the next and with substitutions of other colors. In one example, traffic light style, blue is above average health ($z>0$), green is average health ($-1<z\leq 0$), yellow is average to lower-average health ($-2<z\leq -1$), orange is minor decline ($-3<z<-2$), and red is major decline ($z>-3$).

Example 1

A Set of NPTs is Shown in Table 1.

TABLE 1

| NPTs required for input | | |
|---|---|---|
| # | Test Item Name | Label |
| 1 | Wechsler Logical Memory total | LIMMTOTAL |
| 2 | Wechsler Logical Memory delay total | LDELTOTAL |
| 3 | Wechsler Logical Memory delay queued | LDELCUE |
| 4 | Digit Span Forward score | DSPANFOR |
| 5 | Digit Span Forward length | DSPANFLTH |
| 6 | Digit Span Backward score | DSPANBAC |
| 7 | Digit Span Backward length | DSPANBLTH |
| 8 | Rey's Auditory Verbal Learning total trial 6 | AVTOT6 |
| 9 | Rey's Auditory Verbal Learning errors trial 6 | AVERR6 |
| 10 | Rey's Auditory Verbal Learning 30 minute delay total | AVDEL30MIN |
| 11 | Rey's Auditory Verbal Learning 30 minute delay errors | AVDELERR1 |
| 12 | Rey's Auditory Verbal Learning 30 minute delay recognized on list | AVDELTOT |
| 13 | Rey's Auditory Verbal Learning 30 minute delay errors on list | AVDELERR2 |
| 14 | Boston Naming Test | BNTTOTAL |
| 15 | Categories Animals Score | CATANIMSC |
| 16 | Categories Animals Perseverations | CATANPERS |
| 17 | Categories Animals Intrusions | CATANINTR |
| 18 | Categories Vegetables Score | CATVEGESC |
| 19 | Categories Vegetables Perseverations | CATVGPERS |
| 20 | Categories Vegetables intrusions | CATVGINTR |
| 21 | Trail Making A Score | TRAASCOR |
| 22 | Trail Making A Errors of commission | TRAAERRCOM |
| 23 | Trail Making A Errors of omission | TRAAERROM |
| 24 | Trail Making B Score | TRABSCOR |
| 25 | Trail Making B Errors of commission | TRABERRCOM |
| 26 | Trail Making B Errors of omission | TRABERROM |
| 27 | Digit Symbol Substitution | DIGITSCOR |
| 28 | Mini mental State Exam | MMSCORE |
| 29 | ADAS-COG Q1_WORD_RECALL | ADAS_COG_Q1_WORD_RECALL |
| 30 | ADAS-COG Q2_COMMANDS | ADAS_COG_Q2_COMMANDS |
| 31 | ADAS-COG_Q3_CONSTRUCTION | ADAS_COG_Q3_CONSTRUCTION |
| 32 | ADAS-COG Q4_DEL_WORD_RECALL | ADAS_COG_Q4_DEL_WORD_RECALL |
| 33 | ASAD-COG_Q5_NAMING | ASAD_COG_Q5_NAMING |
| 34 | ADAS-COG Q6_IDEA_PRAXIS | ADAS_COG_Q6_IDEA_PRAXIS |
| 35 | ADAS-COG_Q7_ORIENTATION | ADAS_COG_Q7_ORIENTATION |
| 36 | ADAS-COG Q8_WORD_RECOG | ADAS_COG_Q8_WORD_RECOG |
| 37 | ADAS-COG Q9 RECALL_INSTR | ADAS_COG_Q9_RECALL_INSTR |
| 38 | ADAS-COG_Q10_SPOKEN_LANG | ADAS_COG_Q10_SPOKEN_LANG |
| 39 | ADAS-COG Q11 WORD_FINDING | ADAS_COG_Q11_WORD_FINDING |
| 40 | ADAS-COG Q12 COMPREHENSION | ADAS_COG_Q12_COMPREHENSION |
| 41 | ADAS-COG_Q14_NUMBER_CANCEL | ADAS_COG_Q14_NUMBER_CANCEL |
| 42 | ADAS-COG TOTAL11 | ADAS_COG_TOTAL11 |
| 43 | ADAS-COG_TOTALMOD | ADAS_COG_TOTALMOD |
| 44 | CLOCK_DRAW | CLOCK_DRAW |
| 45 | CLOCK_COPY | CLOCK_COPY |

In Table 1, ADAS-Cog represents Alzheimer's Disease Assessment Scale—Cognitive Subscale.

Example 2

Raw scores are first corrected for the influences of gender, race, age, and years of education when these factors were found to be significant in the cohort of stable normal controls in the ADNI study. The resulting corrections are summarized in Table 2.

TABLE 2

| Summary of z-score corrections | |
|---|---|
| Label | Correction model |
| LIMMTOTAL | gender, edu |
| LDELTOTAL | gender, race, edu |
| LDELCUE | none |
| DSPANFOR | age, edu |
| DSPANFLTH | edu |
| DSPANBAC | edu |
| DSPANBLTH | edu |

TABLE 2-continued

Summary of z-score corrections

| Label | Correction model |
|---|---|
| AVTOT6 | none |
| AVERR6 | none |
| AVDEL30MIN | none |
| AVDELERR1 | none |
| AVDELTOT | gender, rage, edu |
| AVDELERR2 | gender, edu |
| BNTTOTAL | gender, edu |
| CATANIMSC | edu |
| CATANPERS | none |
| CATANINTR | gender, race |
| CATVEGESC | gender |
| CATVGPERS | none |
| CATVGINTR | gender, age |
| TRAASCOR | gender, race, age, edu |
| TRAAERRCOM | gender, race, age, edu |
| TRAAERROM | none |
| TRABSCOR | age, edu |
| TRABERRCOM | gender, race, age |
| TRABERROM | none |
| DIGITSCOR | gender, age, edu |
| MMSCORE | gender, race, age, edu |
| ADAS_COG_Q1_WORD_RECALL | gender |
| ADAS_COG_Q2_COMMANDS | none |
| ADAS_COG_Q3_CONSTRUCTION | edu |
| ADAS_COG_Q4_DEL_WORD_RECAL | gender |
| ASAD_COG_Q5_NAMING | gender, race, edu |
| ADAS_COG_Q6_IDEA_PRAXIS | none |
| ADAS_COG_Q7_ORIENTATION | none |
| ADAS_COG_Q8_WORD_RECOG | none |
| ADAS_COG_Q9_RECALL_INSTR | none |
| ADAS_COG_Q10_SPOKEN_LANG | none |
| ADAS_COG_Q11_WORD_FINDING | age |
| ADAS_COG_Q12_COMPTEHENSION | none |
| ADAS_COG_Q14_NUMBER_CANCEL | age |
| ADAS_COG_TOTAL11 | none |
| ADAS_COG_TOTALMOD | gender |
| CLOCK_DRAW | gender, race, age, edu |
| CLOCK_COPY | gender, age, edu |

The mean and standard deviation (sd) of each corrected item was computed for the baseline visit for the cohort of stable normal controls and used to convert all corrected scores to Z-scores using the formula $Z=(raw-mean)/sd$.

In order to correct for the fact that a high score indicates better cognitive performance for some items, while the opposite is true for other items, e.g. counts of errors, some items were inverted [using (mean−raw) instead of (raw−mean)] so that all Z-scores can be interpreted such that lower scores indicate worse cognitive performance. Clinically, a score of −1, which is one sd below the NL mean, indicates a cognitive deficit, and scores below −1.5 or −2 represent significant cognitive deficit.

Example 3

In an exemplary embodiment, a set of decision trees is shown below, which use the input data z-scores described above. Using these corrected Z-scores, each of the twenty-five (25) decision trees returns an output value of zero (0), which represents no conversion from MCI to AD, or an output value of one (1), which represents conversion from MCI to AD. The patient threshold value, n, is the sum of the output values for the twenty-five (25) decision trees.

All publications, references, patents, patent publications and patent applications cited herein are each hereby specifically incorporated by reference in their entirety for all purposes.

While certain embodiments, aspects, or variations have been described, and many details have been set forth for purposes of illustration, it will be apparent to those skilled in the art that additional embodiments, aspects, or variations may be contemplated, and that some of the details described herein may be varied considerably without departing from what is described herein. Thus, additional embodiments, aspects, and variations, and any modifications and equivalents thereof which are understood, implied, or otherwise contemplated are considered to be part of the invention(s) described herein. For example, the present application contemplates any combination of the features, terms, or elements of the various illustrative components and examples described herein.

The use herein of the terms "a," "an," "the" and similar terms in describing the invention, and in the claims, are to be construed to include both the singular and the plural, for example, as "one or more."

The terms "comprising," "having," "include," "including" and "containing" are to be construed as open-ended terms which mean, for example, "including, but not limited to." Thus, terms such as "comprising," "having," "include," "including" and "containing" are to be construed as being inclusive, not exclusive.

The examples given herein, and the exemplary language used herein are solely for the purpose of illustration, and are not intended to limit the scope of the invention. All examples and lists of examples are understood to be non-limiting.

What is claimed is:

1. A method for selecting a cohort group or a patient at risk from a population of patients with mild cognitive impairment, the method comprising using a computer configured to perform the steps:
    receiving normalized learning data from a portion of the population of patients;
    tuning a set of decision trees on the normalized learning data;
    receiving patient data from one or more patients of the population, wherein the patient data is independent from the learning data;
    classifying the patient data with the tuned set of decision trees to obtain patient threshold values, the patient threshold value being the number of decision trees in the set of tuned decision trees that classify the patient as a mild cognitive impairment to Alzheimer's disease converter; and
    displaying the patient threshold values.

2. The method of claim 1, further comprising selecting a cohort group or a patient at risk from the population, wherein the selected cohort group or patient at risk is outside the portion of the population that supplied the learning data, and the cohort group or patient at risk is selected for a medical purpose based on the patient threshold values.

3. The method of claim 2, wherein the cohort group or patient at risk is selected for the medical purpose of at least one of performing a clinical study relating to Alzheimer's and treating the patients for Alzheimer's.

4. The method of claim 2, wherein the cohort group or patient at risk is selected for the medical purpose of determining at least one of a drug to be administered for treating the patients for Alzheimer's and a dosage of the drug to be administered for treating the patients for Alzheimer's.

5. The method of claim 1, wherein the patient threshold values am displayed in a receiver operating curve, and wherein tuning the set of decision trees determines a numerical range of a number of boosting iterations, a numerical range of a minimum number of patients in a node to be split, and a numerical range of a maximum node depth, thereby providing a set of decision trees having at least 85% accuracy for the learning data.

6. The method of claim 5, wherein the range of the number of boosting iterations is 25 or greater.

7. The method of claim 5, wherein the range of the number of boosting iterations is from 25 to 200.

8. The method of claim 5, wherein the range of the minimum number of patients in a node to be split is from 12 to 40.

9. The method of claim 5, wherein the minimum number of patients in a node to be split is 24.

10. The method of claim 5, wherein the range of the maximum node depth is from 6 to 15.

11. A method for selecting a cohort group or a patient at risk from a population of patients with mild cognitive impairment the method comprising using a computer configured to perform the steps:
receiving normalized learning data from a portion of the population of patients;
tuning a set of decision trees on the normalized learning data;
receiving patient data from one or more patients of the population, wherein the patient data is independent from the learning data;
classifying the patient data with the tuned set of decision trees to obtain patient threshold values; and
displaying the patient threshold values;
the learning data comprising:
a first learning data set obtained from the population of patients with mild cognitive impairment, wherein the patients from whom the first learning data set is obtained are observed to convert to Alzheimer's within six months to two years after the first learning data set is obtained, the first learning data set comprising neuropsychological test results and biomarkers; and
a second learning data set obtained from patients in the population of patients with mild cognitive impairment who do not convert to Alzheimer's within six months to two years after the second learning data set is obtained, the second learning data set comprising neuropsychological test results and biomarkers,
wherein the biomarkers are obtained from medical imaging, PET imaging, or MRI imaging,
and
wherein the biomarkers are molecular biomarkers, CSF biomarkers, or blood sample biomarkers.

12. The method of claim 1, the patient data comprising data obtained from patients in the population of patients with mild cognitive impairment, and comprising neuropsychological test results and biomarkers, wherein the biomarkers are obtained from medical imaging, PET imaging, or MRI imaging, and wherein the biomarkers are molecular biomarkers, CSF biomarkers, or blood sample biomarkers.

13. The method of claim 1, further comprising a step of administering a drug for treating Alzheimer's Disease to the cohort group or the patient at risk.

14. A computer programmed to perform a method for selecting a cohort group or a patient at risk from a population of patients with mild cognitive impairment, the method comprising the steps;
receiving normalized learning data from a portion of the population of patients;
tuning a set of decision trees on the normalized learning data;
receiving patient data from one or more patients of the population, wherein the patient data is independent from the learning data;
classifying the patient data with the tuned set of decision trees to obtain patient threshold values, the patient threshold value being the number of decision trees in the set of tuned decision trees that classify the patient as a mild cognitive impairment to Alzheimer's disease converter; and
displaying the patient threshold values.

15. The computer of claim 14, the method further comprising selecting a cohort group or a patient at risk from the population, wherein the selected cohort group or patient at risk is outside the portion of the population that supplied the learning data, and the cohort group or patient at risk is selected for a medical purpose based on the patient threshold values.

* * * * *